US00PP23190P2

(12) United States Plant Patent
Chen

(10) Patent No.: US PP23,190 P2
(45) Date of Patent: Nov. 13, 2012

(54) ***CORDYLINE* PLANT NAMED 'SPRICORFANTASY'**

(50) Latin Name: *Cordyline australis*
Varietal Denomination: Spricorfantasy

(75) Inventor: Jianping Chen, Zhejiang (CN)

(73) Assignee: Sprint Horticulture Pty. Ltd., Wamberal, NSW (AU)

( * ) Notice: Subject to any disclaimer, the term of this patent is extended or adjusted under 35 U.S.C. 154(b) by 0 days.

(21) Appl. No.: 13/135,604

(22) Filed: Jul. 8, 2011

(51) Int. Cl.
*A01H 5/00* (2006.01)

(52) U.S. Cl. ..... Plt./383

(58) Field of Classification Search ..... Plt./383
See application file for complete search history.

*Primary Examiner* — Kent L Bell

(74) *Attorney, Agent, or Firm* — C. A. Whealy

(57) ABSTRACT

A new and distinct cultivar of *Cordyline* plant named 'Spricorfantasy', characterized by its upright to semi-erect habit with foliage initially erect to outwardly arching; vigorous growth habit; long lanceolate variegated leaves with green, yellow white and pale yellow-colored longitudinal stripes and greyed orange coloration towards the base; and excellent keeping quality and good garden performance.

2 Drawing Sheets

Botanical designation: *Cordyline australis*.
Cultivar denomination: 'SPRICORFANTASY'.

BACKGROUND OF THE INVENTION

The present invention relates to a new and distinct *Cordyline* plant, botanically known as *Cordyline australis* and hereinafter referred to by the name 'Spricorfantasy'.

The new *Cordyline* plant is a naturally-occurring whole plant mutation of the *Cordyline australis* 'Torbay Dazzler', not patented. The new *Cordyline* plant was discovered and selected by the Inventor from within a population of plants of 'Torbay Dazzler' in a controlled greenhouse environment in Zhejiang, China in March, 2009.

Asexual reproduction of the new *Cordyline* plant by micropropagated cuttings in Zhejiang, China since March, 2009 has shown that the unique features of this new *Cordyline* plant are stable and reproduced true to type in successive generations.

SUMMARY OF THE INVENTION

Plants of the new *Cordyline* have not been observed under all possible environmental conditions and various cultural practices. The phenotype may vary somewhat with variations in environmental conditions such as temperature and light intensity, without, however, any variance in genotype.

The following traits have been repeatedly observed and are determined to be the unique characteristics of 'Spricorfantasy'. These characteristics in combination distinguish 'Spricorfantasy' as a new and distinct *Cordyline* plant:

1. Upright to semi-erect plant habit with foliage initially erect to outwardly arching.
2. Vigorous growth habit.
3. Long lanceolate variegated leaves with green, yellow white and pale yellow-colored longitudinal stripes and greyed orange coloration towards the base.
4. Excellent keeping quality and good garden performance.

Plants of the new *Cordyline* differ from plants of the parent, 'Torbay Dazzler', primarily in leaf size as plants of 'Torbay Dazzler' have broader leaves than plants of the new *Cordyline*. In addition, plants of the new *Cordyline* and 'Torbay Dazzler' differ in leaf color as plants of 'Torbay Dazzler' have green and yellow variegated leaves with red-colored leaf bases.

Plants of the new *Cordyline* can be compared to plants of the *Cordyline australis* 'Pink Champagne', not patented. In side-by-side comparisons conducted in Wamberal, New South Wales, Australia, plants of the new *Cordyline* differed primarily from plants of 'Pink Champagne' in the following characteristics:

1. Plants of the new *Cordyline* had narrower leaves than plants of 'Pink Champagne'.
2. Leaves of plants of the new *Cordyline* and 'Pink Champagne' differed in coloration as plants of 'Pink Champagne' had leaves with pink-colored bases.

BRIEF DESCRIPTION OF THE PHOTOGRAPHS

The accompanying photographs illustrate the overall appearance of the new *Cordyline* plant showing the colors as true as it is reasonably possible to obtain in colored reproductions of this type. Colors in the photographs may differ slightly from the color values cited in the detailed botanical description which accurately describe the colors of the new *Cordyline* plant.

The photograph on the first sheet comprises a side perspective view of a typical plant of 'Spricorfantasy' grown in a container.

The photograph on the second sheet is a top perspective view of typical plants of 'Spricorfantasy' grown in containers.

DETAILED BOTANICAL DESCRIPTION

The aforementioned photographs and following observations and measurements describe plants grown during the summer and autumn in 20-cm containers in an outdoor nursery in Wamberal, New South Wales, Australia and under conditions and practices which approximate those generally used in commercial *Cordyline* plant production. During the production of the plants, day temperatures ranged from 20° C. to 35° C. and night temperatures ranged from 10° C. to 18° C. Plants were 13 months old when the photographs and the botanical description were taken. In the following description, color references are made to The Royal Horticultural Society Colour Chart, 2007 Edition, except where general terms of ordinary dictionary significance are used.

Botanical classification: *Cordyline australis* 'Spricorfantasy'.

Parentage: Naturally-occurring whole plant mutation of *Cordyline australis* 'Torbay Dazzler', not patented.

Propagation:

*Type*.—By micropropagated cuttings.

*Time to initiate roots, summer*.—About 7 to 10 days at temperatures of about 20° C. to 25° C.

*Time to initiate roots, winter*.—About 10 to 14 days at temperatures of about 15° C. to 20° C.

*Time to produce a rooted young plant, summer*.—About 25 to 30 days at temperatures of about 20° C. to 25° C.

*Time to produce a rooted young plant, winter*.—About 35 to 40 days at temperatures of about 15° C. to 20° C.

*Root description*.—Medium thickness, fibrous; white in color.

*Rooting habit*.—Moderately freely branching; medium density to dense.

Plant description:

*Plant and growth habit*.—Upright to semi-erect habit with foliage initially erect to outwardly arching; broadly inverted triangle; non-branching habit; moderately vigorous growth habit.

*Plant height*.—About 75 cm.

*Plant diameter or spread*.—About 85 cm.

Foliage description:

*Orientation*.—Initially erect to outwardly arching.

*Arrangement*.—Whorled; sessile.

*Length*.—About 45 cm to 75 cm.

*Width*.—About 1 cm to 1.6 cm.

*Shape*.—Lanceolate.

*Apex*.—Acute.

*Margin*.—Entire.

*Cross-sectional profile*.—Towards the base, concave, flattening slightly towards the apex.

*Texture, upper and lower surfaces*.—Leathery; corrugated, glabrous.

*Luster, upper and lower surfaces*.—Moderately glossy.

*Venation pattern*.—Parallel.

*Color*.—Developing leaves, upper and lower surfaces: Close to 146C to 146D. Fully expanded leaves, upper and lower surfaces: Primary color, central longitudinal stripes, close to 146A; marginal longitudinal stripes, towards the base, close to 164B to 164D; marginal longitudinal stripes, center of leaf, close to 158A to 158B; marginal longitudinal stripes, towards the apex, close to 11C; towards the base, stripes are tinted with close to 164A and distally tinted with close to 176C to 176D. Venation, upper and lower surfaces: Similar to surface coloration.

Flower description: Flower initiation and development has not been observed on plants of the new *Cordyline*.

Disease/pest resistance: Plants of the new *Cordyline* have not been shown to be resistant to pathogens and pests common to *Cordyline*.

Keeping quality: Excellent keeping quality; plants of the new *Cordyline* are durable and will maintain good leaf substance indefinitely.

Garden performance: Plants of the new *Cordyline* have been observed to have good garden performance and to tolerate wind, rain and high temperatures of about 40° C. Low temperature tolerance has not been determined.

It is claimed:

1. A new and distinct *Cordyline* plant named 'Spricorfantasy' as illustrated and described.

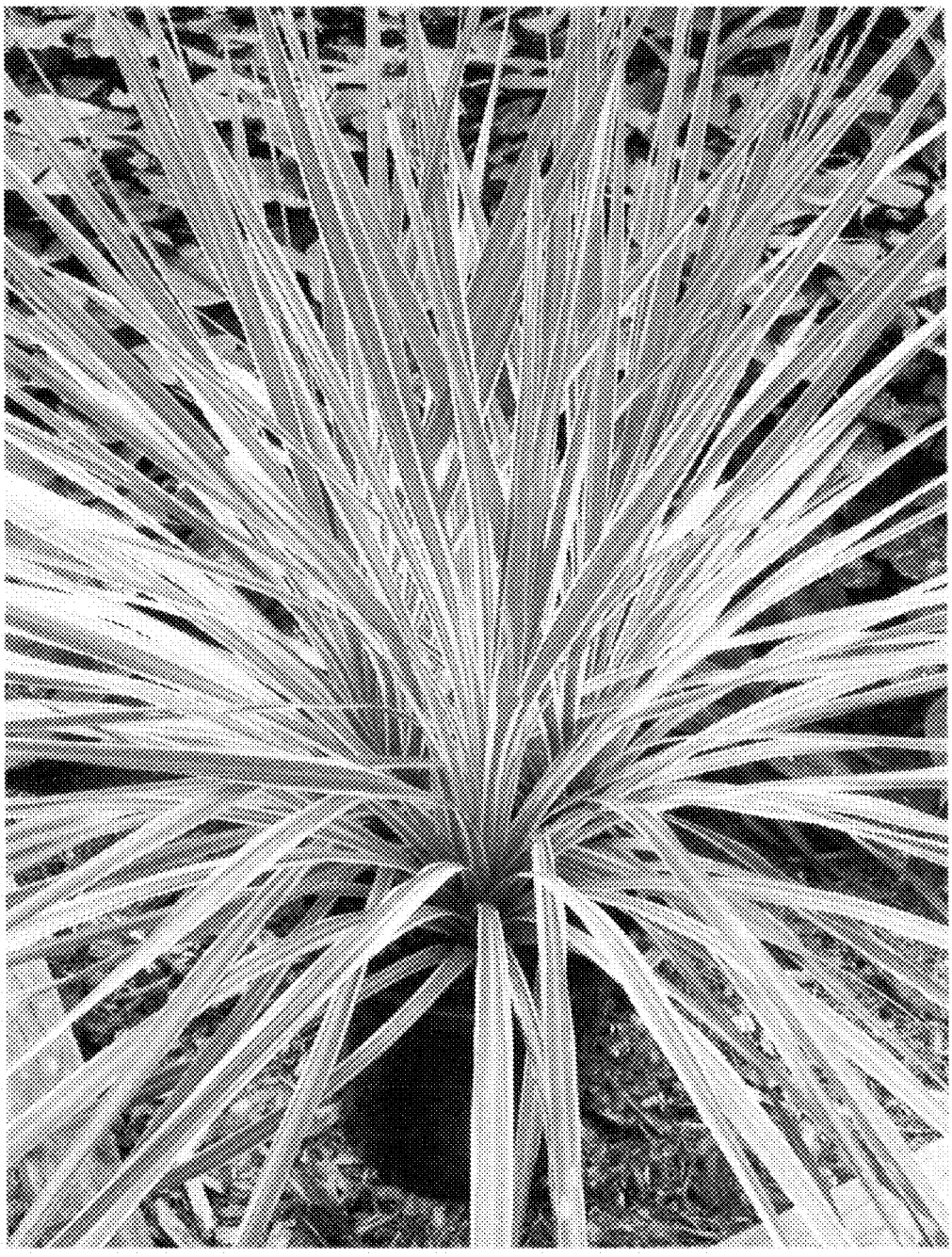

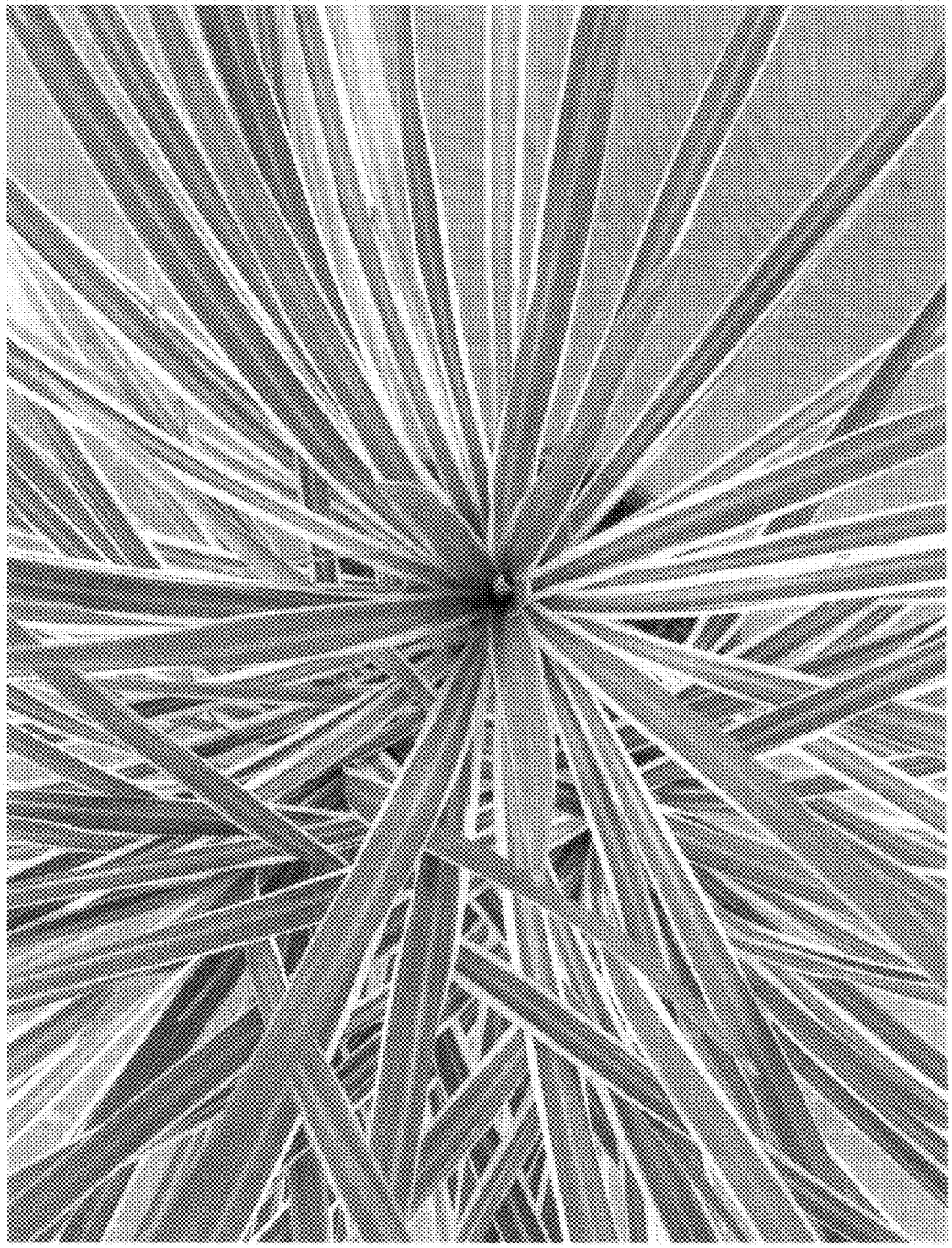

* * * * *